US006299608B1

(12) United States Patent
Solomon et al.

(10) Patent No.: US 6,299,608 B1
(45) **Date of Patent: *Oct. 9, 2001**

(54) TRANSFER ASSEMBLY FOR PROVIDING A STERILITY SEAL IN A MEDICINAL STORAGE BOTTLE

(75) Inventors: Donald D. Solomon, Warwick, NY (US); Jean-Claude Thibault, Saint-Egreve (FR)

(73) Assignee: Becton Dickinson France, S.A., Le Pont (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/138,135

(22) Filed: Aug. 21, 1998

Related U.S. Application Data

(60) Continuation of application No. 08/754,824, filed on Nov. 21, 1996, now Pat. No. 5,855,575, which is a division of application No. 08/377,885, filed on Jan. 25, 1995, now Pat. No. 5,613,291.

(51) Int. Cl.$^{7}$ ..................................................... A61B 19/00

(52) U.S. Cl. .......................... 604/411; 604/403; 604/404; 604/405; 604/406; 604/407; 604/411; 604/412; 604/413; 604/414; 604/415; 604/905; 215/341; 215/346; 215/352

(58) Field of Search ..................................... 604/403–407, 604/411, 412, 413, 414–415, 905; 206/219, 222, 419, 420

(56) References Cited

U.S. PATENT DOCUMENTS 3,206,073 * 9/1965 Scislowicz ............................. 222/80
5,358,501 * 10/1994 Meyer .................................. 604/414
6,019,750 * 2/2000 Fowles et al. ........................ 604/403
6,022,339 * 2/2000 Fowles et al. ........................ 604/411
6,209,738 * 4/2001 Hansen et al. ........................ 215/247

* cited by examiner

*Primary Examiner*—Aaron J. Lewis
*Assistant Examiner*—Michael Bogart
(74) *Attorney, Agent, or Firm*—Allen W. Wark

(57) ABSTRACT

A bottle having a sterility seal and a method for producing same are disclosed. The bottle, which can be configured to retain a medicament in powder or tablet form, features a protective cap configured to engage a transfer assembly associated with the bottle. The cap includes one or more raised ridges on an interior surface engageable with a portion of the transfer assembly. A band or layer configuration of a sealing material such as silicone is applied to the transfer assembly prior to insertion of the cap thereover. As the cap comes into surface contact with the sealing material, the ridges cause the material to "roll up" into a toroidal O-ring configuration, thereby forming a seal between the cap and the bottle adapted to the dimensional variations of those components. The seal, which is resilient, is able to withstand harsh handling treatment and pressure or temperature variations without separation from the cap or bottle, thereby providing a hermetic seal isolating the transfer assembly and, hence, the medicament from the outside environment.

15 Claims, 4 Drawing Sheets

TRANSFER ASSEMBLY FOR PROVIDING A STERILITY SEAL IN A MEDICINAL STORAGE BOTTLE

This is a continuation of application Ser. No. 08/754,824, filed Nov. 21, 1996, now U.S. Pat. No. 5,855,575, which is a divisional of application Ser. No. 08/377,885, filed Jan. 25, 1995, now U.S. Pat. No. 5,613,291.

FIELD OF THE INVENTION

The invention relates to a method and apparatus for providing sterility in a medicinal storage bottle, and more particularly, to a method and apparatus for creating a sterility seal in a medicinal bottle impervious to disruptions by tolerance difficulties or shipping treatment.

BACKGROUND

In the medical arts, there are known certain medicinal storage bottles useful for storing, shipping and containing a medicine disposed in dry powder or tablet form that is intended to be reconstituted with a liquid substance for administration to a patient. Examples of such containers are found, inter alia, in U.S. Pat. Nos. 3,033,202 to Richter et al.; 3,206,073 to Scislowicz; 4,211,333 to Villarejos; and 4,941,876, 5,358,501 and PCT Application WO 90/07319, all to Meyer or Meyer et al. Utilizing the Scislowicz patent as a reference and as depicted in FIGS. 1 and 2 of that patent, common to all the devices disclosed in the prior art there includes some type of container 10 containing a medicament 14 to be reconstituted. Access to a reconstituting fluid 37 held in a separate container 35 is provided by a transfer assembly 13. In the Scislowicz reference, the transfer assembly includes a sharpened cannula element, but in the case of the Meyer et al. U.S. '876 and PCT '319 references, the transfer assembly includes some type of Luer-Lock adapter suitable for connection directly with other bottles (for instance, PCT '319) or with a separate needle cannula element (U.S. '876).

As the skilled artisan will appreciate, the sterility of the medicinal component 14 held in the container 10 is normally preserved by some type of sealing mechanism, isolating at least the medicament 14 from contamination with the outside environment. In a number of these assemblies, such as the Scislowicz '073 patent or the Meyer '501 patent, sealing isolation for the medicament is provided by incorporating as part of the transfer assembly some type of sealing mechanism slidably engageable with the neck of the bottle, itself incorporating a fluid conduit selectably in fluid communication with the interior of the bottle. The transfer assembly can thus be slid downwards towards the interior of bottle when reconstitution of the medicament is desired. However, during transport of the bottle, the sealing portion is retained in the neck, in an attempt to block the fluid conduit and cut off any environmental contact with the interior of the bottle through the transfer assembly.

In a similar vein, separate seal portions are often incorporated about the transfer assembly to further enhance the imperviousness of the aforementioned designs to extraneous contamination. For example, in the Meyer '501 patent, a toroidally-shaped sealing element 29 is incorporated which contacts the interior neck portion of the container 10 so as to form an aseptic barrier during storage, as well as to provide a sealed connection and an aseptic barrier during the activation phase of the container. In addition, as evident from the Scislowicz or Meyer references, a removable cap element 40 is often fitted about the transfer assembly 13 in an effort to protect the transfer assembly from damage or contaminating contact pending use of the container. The cap, often configured to be retained with or against a portion of the container 10, can be covered with a tamper-evident seal (such as seen in Meyer '501) so as to give further indication if the sterility of the medicament 14 might have been somehow compromised.

While the foregoing approaches in general are directed to preserving the sterility of the medicament 14 held within the container, discrepancies in dimensions or manufacturing tolerances of the various components forming the medicinal storage bottles, the handling of the bottles during shipment by ground, sea or air, and related factors could affect the ability of the bottles to maintain sterility of the medicament 14 pending use. Tests for integrity include, inter alia, immersing the bottle in a fluid bath over a set period of time, with the fluid held at pressures simulating conditions to which the bottle will be exposed over time.

In particular, while for the most part serving to isolate the medicament itself from external contaminant effects, it has been found that contaminants of liquid, biological, or particulate nature may still be able to infiltrate the container through the cap element 40, thereby contaminating the transfer assembly 13. Difficulties associated with molding the interface between cap and container with a perfectly precise fit make it virtually impossible to ensure sterility relying solely on the cap as a barrier. More specifically, dimensional variations are bound to occur from production batch to batch, so that a hermetic seal between matching components cannot be assured in every instance. In addition, molded parts sometimes display weld lines which, if disposed in an area necessitating perfect mating contact, can interfere with precise fit. Overall then, most molding techniques cannot be relied upon to produce seals of a hermetic nature. This, more often than not, is an unacceptable condition for a product relying on sterility prior to use.

The above-mentioned difficulties are further amplified by the treatment imposed on the bottles during shipment. For example, the bottles may be exposed to extreme atmospheric variations, inclusive of temperature extremes and, when shipment occurs by air, significant pressure disturbances. Such changes in pressure or temperature act upon the individual components and normally cause any hermetic seals effected by precision molding to be disrupted or broken, exposing the bottle and particularly the transfer assembly to contamination. Absent a proper seal impervious to atmospheric variations, shipment is oftentimes limited to road or rail transport, which is slower and sometimes costlier than shipment by air.

Moreover, owing to considerations of cost, manufacturing efficiencies, and ease of transport, it is common for relatively bulky items such as medicinal storage bottles to be shipped only in simple corrugated or cardboard containers, which provide little if any protection against exposure to outside contaminants. Blister packs or pouches, typically employed when an enclosed product is sterilized such as by gas treatment or irradiation, are normally excluded from bulky product such as medical storage bottles. Thus, there is usually the requirement for the bottle to rely solely on its own integral design and its components for maintaining the sterility of the product contained therein.

There is a need, therefore, for a way to ensure sterility in a medicinal storage bottle, relying on its integral componentry and design, which is particularly impervious to handling or shipment conditions to which the bottle is exposed, and which accounts for tolerance or dimensional variations in the components forming the bottle.

SUMMARY OF THE INVENTION

These and other concerns are addressed by a method and apparatus for providing a sterility seal in a medicinal storage bottle in accordance with the present invention. A sterility seal, formed from a particulate, gaseous or aqueous impervious sealing material, is precisely located between the protective cap and the bottle in a manner so as to isolate the transfer assembly from outside contaminants.

In one embodiment, a band or layer configuration of a sealing material such as silicone is applied to a circumferential zone of the bottle that is subject to contact with the interior of the cap. Application may be effected, for instance, by a sponge or foam applicator disposed in rotating contact with the bottle. The interior of the cap is structured to include one or more ridge-type elements in an area coming into contact with the zone of silicone application. In one embodiment, the sealing material is applied to the bottle in a base area of the transfer assembly adjacent the container portion of the bottle, with the ridge elements formed for contact with the base area of the transfer assembly.

Upon insertion of the cap over the bottle, the ridge-type elements are urged into contact with the layer of silicone, causing the band of silicone to roll downwards along the surface of the transfer assembly so as to "bunch" into a toroidally-shaped O-ring type seal precisely conforming to the dimensions of the cap and storage bottle. The seal "caulks" any gaps or openings (collectively "microsurface defects") between the cap and the bottle created, for instance, by imprecise molding, handling treatment, or environmental variations, thereby hermetically isolating the transfer assembly from the outside environment so as to preserve the sterility of same. A reliable seal is thus created which is rupturable only by the user prior to administration of the medicament contained in the bottle. Owing to good surface tension as well as the resiliency properties of the sealing material, the seal created is able to withstand abuses rendered to the bottle by handling treatment as well as the stresses and strains imposed by environmental changes without rupture or separation from the cap or bottle, thereby better assuring the sterility of the bottle and the contents held therein.

BRIEF DESCRIPTION OF THE DRAWINGS

The invention will now be described in greater detail by way of reference to the following drawings, wherein.

DETAILED DESCRIPTION OF THE INVENTION

Figure 1:
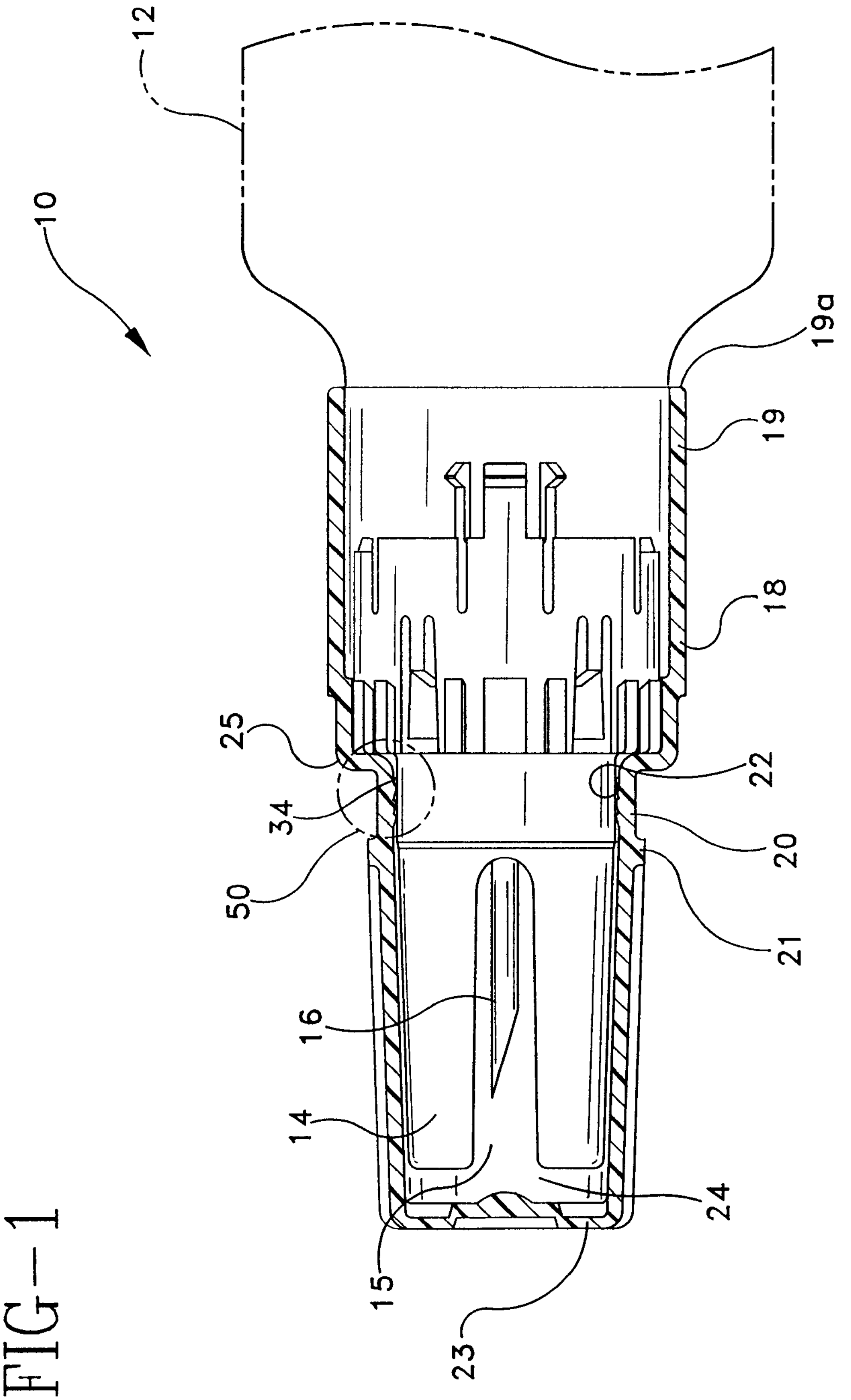
FIG. 1 is a cutaway view of a medicinal storage bottle in accordance with the present invention, illustrating the relationship between the bottle, the transfer assembly, the protective cap and the seal.
Figure 3:
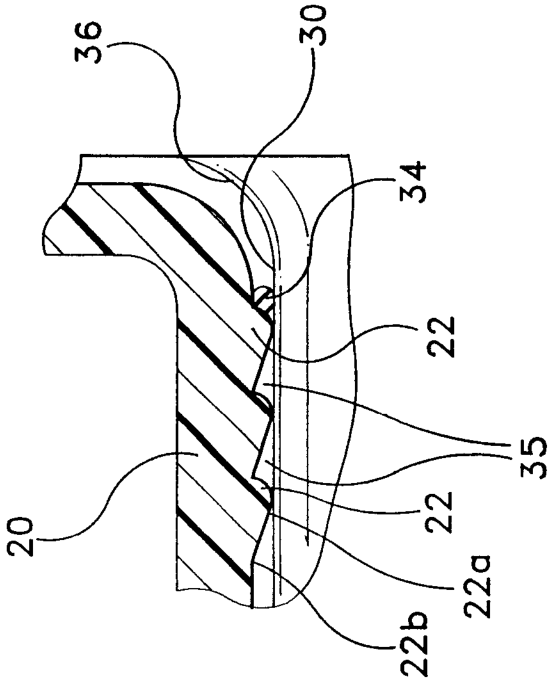
FIG. 3 is a cutaway view illustrating the relationship between the protective cap and the transfer assembly following placement of the cap, together with the formation of a seal between the cap and the transfer assembly.
Figure 2:
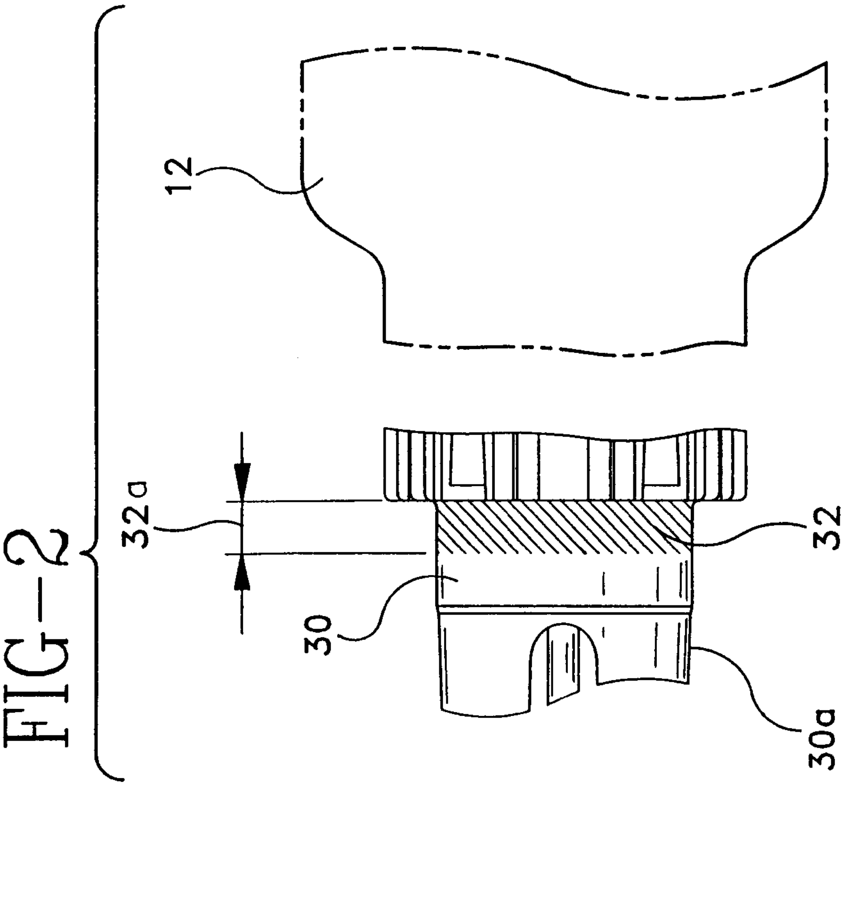
FIG. 2 is a cutaway view of the transfer assembly of the medicinal storage bottle illustrating the band configuration of sealing material following application.

Turning now to the drawings, wherein like numerals denote like components, FIGS. 1 through 3 illustrate one embodiment of a medicinal storage bottle 10 in accordance with the present invention. The various components of the medicinal storage bottle can be formed or molded from conventional materials known to artisan in the medical arts, such as polypropylene, polycarbonate polyethylene, glass, or the like. The bottle 10 typically includes a container portion 12 adapted to retain therein a substance such as dry powder medicaments or tablet form medicaments or lyophilized medicaments intended for reconstitution. A transfer assembly portion 14, adapted for fluid communication with the container portion 12, is normally provided so as to provide reconstituting fluid to the medicament held within the container portion 12 as well as deliver the reconstituted medicament to a patient.

As here illustrated, the transfer assembly 14 is generally formed in a cylindrical shape that defines an interior area 15 surrounding a piercing element 16 such as a sharpened needle cannula. The piercing element 16 is in fluid communication with the container 12 and serves to transmit fluid to and from the container 12. As will be understood by the skilled artisan, the transfer assembly 14 may take any variety of shapes or configurations as need or desire dictate (for instance, a square configuration), and the piercing element 16 need not be a sharpened needle cannula but can be, for instance, a blunt ended cannula, a luer-type fitting, or other types of fluid transfer devices as employed in the art.

Defining the interior 15 of the transfer assembly, there is a base portion 30 adjacent the container portion 12 of bottle 10, as well as a sidewall portion **30*a* that forms the substantial entirety of the transfer assembly 14. In one configuration, the sidewall portion 30*a* may have an overall length, for instance, of about 24.8 millimeters ("mm") and the base portion 30 can have an overall length of about 7.45 mm. As herein illustrated, the base portion 30 is slightly wider than sidewall portion 30*a*, for purposes to be herein explained. For instance, in one configuration the base portion 30 may display an outside width of about 17.1 mm while the sidewall portion 30*a*** may display an outside width of about 16 mm. However, it will be understood by the skilled artisan that the widths or lengths of the base and sidewall portions can be made identical, or of other differing dimensions, as need or desire dictate.

As illustrated in the figures, a protective cap 18 is provided to safeguard the bottle 10 both from damage as well as contamination pending use of the product. In its form as illustrated, the cap 18 primarily safeguards the transfer assembly 14 from damage as well as contamination with the environment, helping to maintain the sterility of the medicament contained within the container portion 12 until such time as the medicament is accessed for use, and is preferably dimensioned in accordance with the measurements provided the transfer assembly 14. The cap 18 may include a skirt portion 19 lengthened some distance beyond the base portion 30 of the transfer assembly 14 covering or otherwise engageable with the outside surface of the container portion 12 of the bottle; a closed end 23 for covering the exposed end of the transfer assembly 14; and a side wall 21 extending to the leading end **19*a* of the skirt 19 and about the circumference of the cap 18 that defines an enclosed interior portion 24 somewhat larger in diameter than the outside diameter of the sidewall portion 30*a* of the transfer assembly 14. Thus, cap 18 will encapsulate the transfer assembly 14 when placed over the bottle. If desired, a tamper evident seal such as a shrink-wrap seal (not shown) may be applied in contact with the skirt 19 and the container portion 12 subsequent to placement of the cap IS on the bottle 10**.

The cap may feature a contact portion 20 defined between the skirt 19 and the side wall 21, dimensioned to frictionally engage the base portion 30 of the transfer assembly 14 when the cap is placed over the bottle. Owing to the larger diameter of the base portion 30 vis à vis the sidewall portion 30*a* of the transfer assembly, the cap 18 may pass undisturbed over the sidewall portion 30*a* while frictionally engaging the base portion 30. It will be realized that the contact portion 20 may be formed as part of the side wall 21, thereby retaining the same dimensions, or it may be formed wider or larger than the side wall 21 so as to conform to the dimensions of, or portions of, the transfer assembly 14 with which it will engage.

To maximize the barrier properties of the cap, the overall cap 18 is normally preferably dimensioned to be as form fitting as possible with the bottle 10 and/or transfer assembly 14. In this regard, it will be seen that the portions of the cap 18, inclusive of the sidewall 21, skirt 19, and shoulders 25 are preferably molded or otherwise formed to be in as precise dimensional conformity with the bottle 10/transfer assembly 14 as possible. However, as noted hereinabove, current plastic molding technology is of such a state that absolute precision molding of plastic parts to provide perfectly mated surfaces, such as to effect a hermetic seal, is virtually impossible, if not prohibitively cost restrictive in view of the commercial marketplace. Therefore, a need exists for a cost effective way to account for microsurface defects on the mating surfaces of the components so as to seal cap 18 with the bottle 10 against the effects of external contaminants, in a manner to address normal dimensional variations between components or tolerance difficulties therewith.

Thus, FIGS. 1 through 3 illustrate a sealing mechanism 50 provided in accordance with the present invention. Here, one or more ridge elements 22 are molded or otherwise formed in the cap 18 about the contact portion 20 for engagement against the base portion 30 of the transfer assembly 14. If desired, the ridge elements can be formed from the same material as forms the cap 18, or they can be made from a different material as an integral component of the cap itself (for instance, via a co-injection process), or they may be separately formed and attached to the contact portion 20 via adhesives, mechanical affixation techniques or the like. As illustrated, the ridge elements 22 preferably are formed about the circumference of the contact portion 20 and may feature substantially rounded head portions 22*a* engageable with the base portion 30 of the transfer assembly 30. Slanted wall portions 22*b* are also provided which lead either into a following ridge element 22 or directly back to the body of the cap 18. As herein illustrated, there are three ridge elements 22, but it will be understood by the skilled artisan that any number of ridge elements may be provided, i.e., one or more, for the purposes herein described.

Prior to insertion of the cap 18 over the bottle 10, a band or layer configuration of sealing material 32 is applied to the bottle 10, preferably in a region of base portion 30 of the transfer assembly 14 which is subject to engagement with contact portion 20 of the cap 18. As shown, the sealing material 32 is here disposed near the junction of the transfer assembly 14 and the container 12 and substantially cylindrically about the entire circumference of the transfer assembly 14, preferably to effect hermetic sealing of as much of the transfer assembly 14 as possible. Depending on the dimensions of the various components, the band or layer of sealing material 32 may display a width, for instance, of about 3 mm, and is applied in a depth of about 10 micrometers ($\mu$m).

One example of the sealing material 32 which may be employed with the invention is a silicone having a viscosity of 12500 centistokes "ctsk", manufactured by the Dow Corning Corporation under product identification number DC360. It has been found that a silicone having the viscosity properties and the surface tension of this material provide a seal which is thick and strong enough to avoid fluid migration or seal disruption under handling stresses or environmental changes, but still fluid enough to effectively occupy the microsurface defects existent between the cap 18 and the bottle 10 so as to effectively address dimensional variations or tolerance difficulties on the mating surfaces of the components.

Figure 4:
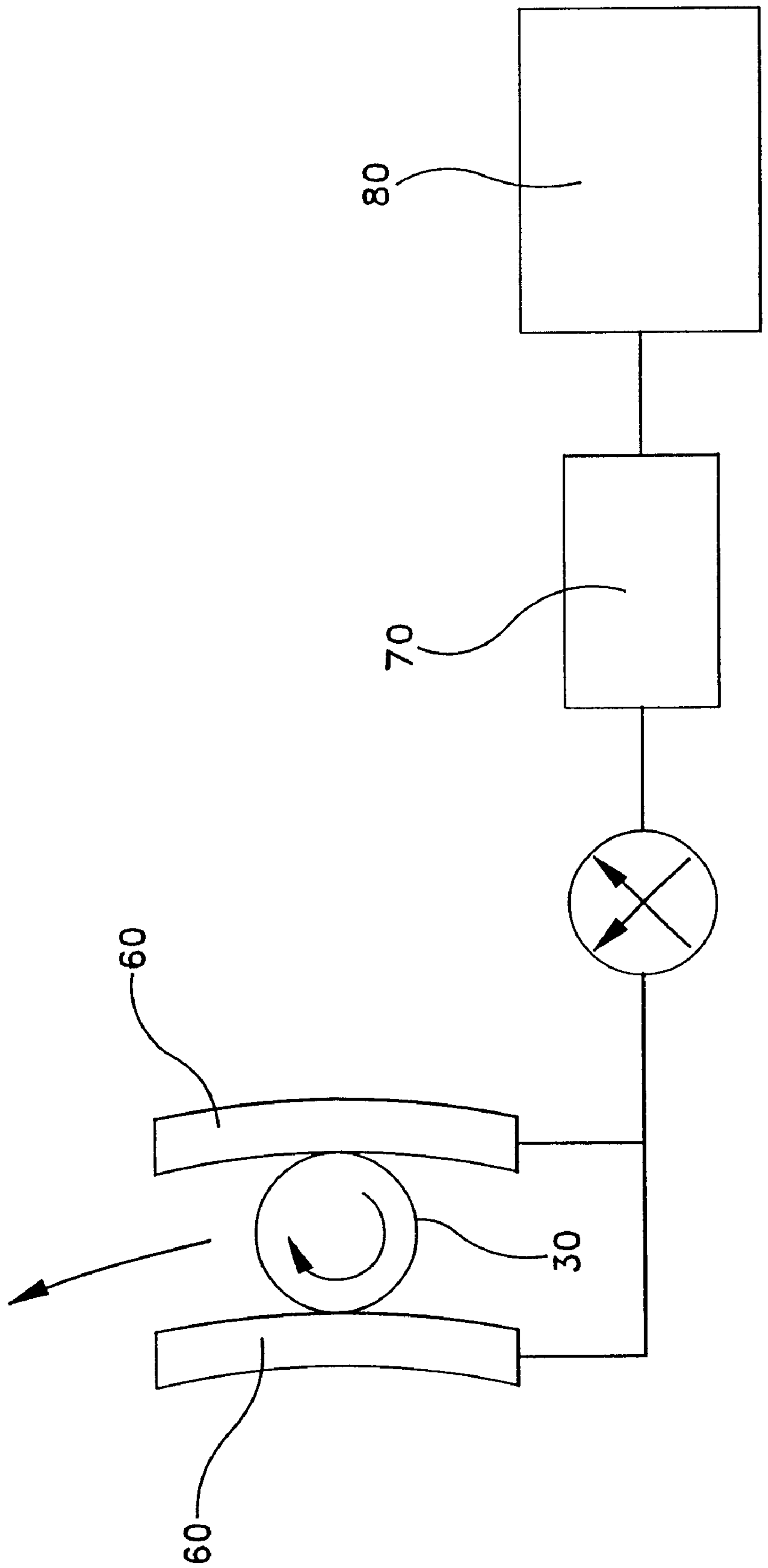
FIG. 4 is a schematic overhead representation of one way to effect application of the sealing material to the bottle.

Numerous ways to effect application of the sealing material within the realm of the skilled artisan are possible As depicted in FIG. 4, one way is to apply the sealing material with an applicator device having foam-like or sponge-like pads 60, appropriately shaped and dimensioned for engagement with the surfaces of the bottle 10 such as base portion 30 of transfer assembly 14, for distribution of the sealing material in a desired width. The pads 60 may display a soft, open cell configuration so as to be well suited to apply the sealing material. For instance, a polyurethane foam having a Shore hardness of about 60–80 may be employed.

The bottle 10 may be rotated against the pads 60 during application so as to uniformly, circumferentially distribute the sealing material 32 into the band configuration desired. The sealing material 32 can be provided from an external source 80 to the foam pads 60 with microdosing pumps 70 which, as the skilled artisan will realize, is a conventional way to ensure a precisely measured, constant, steady supply of material being applied so as to insure both uniformity of application as well as controlling the degree or quantity of application over a given time frame. Other ways to effect application of the sealing material might include, for instance, deposition processes, manual application, projecting the sealing material onto the bottle 10 in a manner similar to "ink jet" printers, or with other techniques known in the art.

Subsequent to the application of the sealing material 32 to the transfer assembly 14, cap 18 may be placed over the bottle 10 in a manner such that the contact portion 20 and, in particular, the head portions 22*a* of the raised elements 22, engage the surface of base portion 30. As the cap is urged downwards over the bottle, the raised elements 22 will engage the sealing material 32 to cause a "rolling" effect as the cap is urged downwards, thereby forming a toroidal-type O-ring seal 34 circumferentially disposed about the base portion 30 and engaging both the base portion 30 and the cap 18. The seal 34 thus created circumferentially conforms to the dimensions of the cap and base portion. The seal which is formed may take the shape of a toroid and serve to perfectly isolate the transfer assembly 14 from the outside environment. Owing to the configuration of the raised elements 22, excess sealing material 32 may "ooze" into the interspaces 35 defined between adjacent raised elements 22 and the base portion 30, enhancing the efficacy of the seal 34 created by the motion of the cap on the sealing material 32, together with providing back-up for the seal 34 so formed.

The seal so produced, thus, is flexible enough to accommodate pressure or temperature variations, together with handling stresses and strains, while effectively blocking gas, particulate or fluid contamination from the transfer assembly. However, by applying an appropriate force on cap 18 such as by twisting the seal may still be readily broken by a user so as to obtain access to the medicament in container portion 12.

Figure 5:
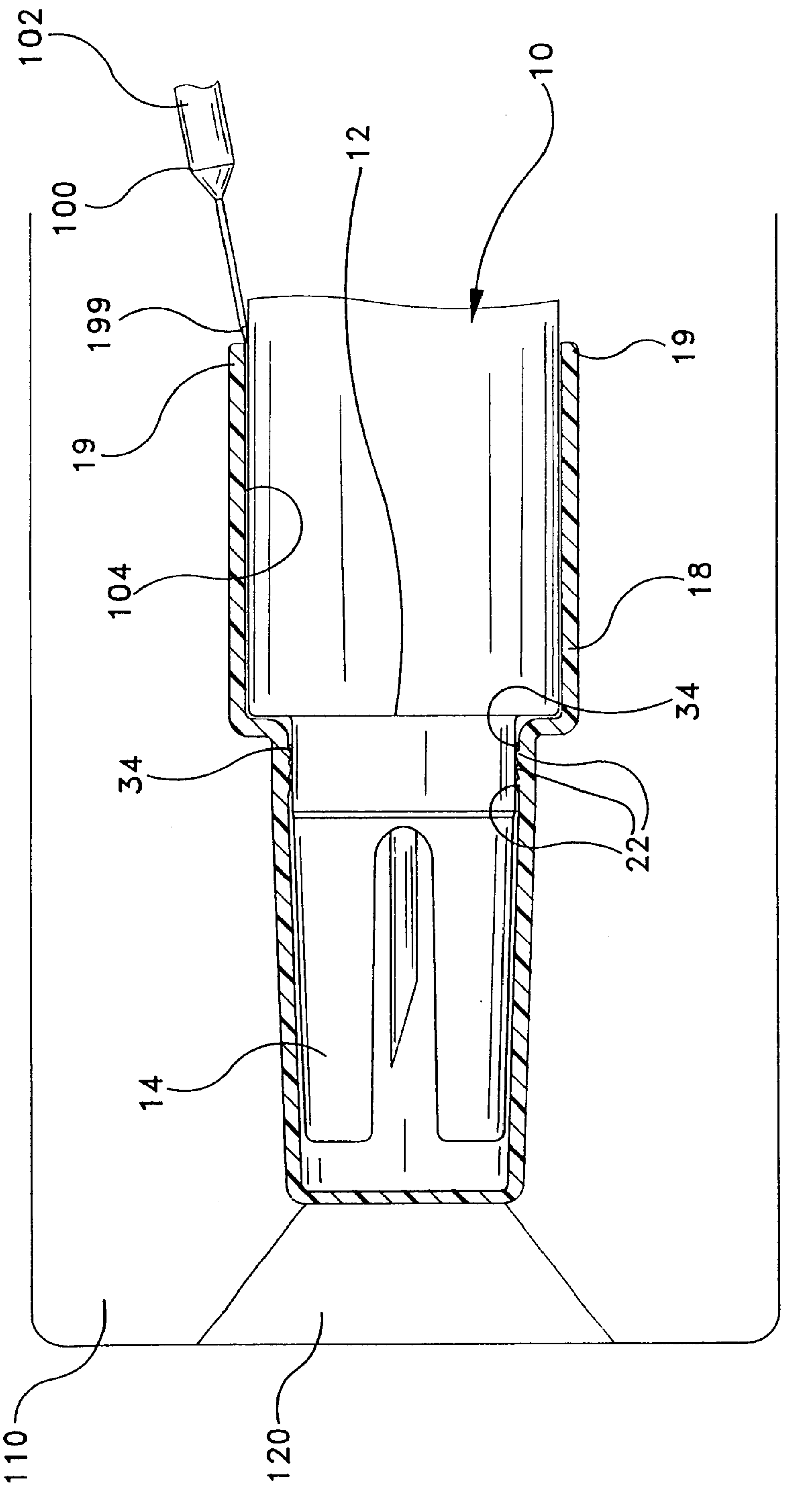
FIG. 5 is a schematic representation of one way to test the efficacy of a seal produced in accordance with the present invention.

The efficacy of a bottle produced in accordance with the present invention is illustrated in a comparison test of four alternative approaches ("Samples 1–4") against two embodiments of a bottle ("Sample 5" and "Sample 6") produced in accordance with the present invention. One test for measuring the efficacy of various bottles against bottle 10 produced in accordance with the present invention is schematically illustrated in FIG. 5. Here, the bottle 10 is tested in a vacuum chamber 110 as known in the art and supported therein by a stand 120. A dye solution 102 containing approximately three percent (3%) methylen blue is injected via syringe 100 into space 104 defined between the skirt 19 and the container portion 12 of the bottle. The bottle 10 is placed upside down so that the dye solution 102 can migrate adjacent the seal 34. The migration of any dye 102 past the seal 34 towards the plurality of raised elements 22 will give an indication of how effective the seal 34 is at preventing contamination.

Subsequent to injection of the dye, the bottle is placed into the chamber 110 and the vacuum pump and regulator of the chamber 110 are regulated in order to achieve an absolute pressure of approximately 0.65 bar. The bottle 10 is held under this condition for approximately sixteen hours, at which point the chamber 110 is returned to atmospheric pressure. The bottle 10 is then removed from the chamber and observations are made, beginning at 30 minute intervals, to determine the migration of the dye 102 past the seal 34 and the three raised elements 22 so as to gauge the efficacy of the device.

Believing that the cap 18 could by itself perform two distinct functions—retain itself onto the transfer assembly 14 with a force low enough so as not to impede a user's easy removal when desired, while also resealing the transfer assembly against contamination—attempts were made to optimize the fit between the cap and the bottle by "tweaking" either of the cap mold or the bottle mold. "Sample 1" and "Sample 2" thus represent, respectively, samples of bottles produced prior to any attempt to correct tolerance difficulties or dimensional difficulties, Sample 1 being a bottle produced prior to stabilization of the bottle molds by the mold maker, and Sample 2 representing a bottle produced by a molder attempting to control molding cycles so as to obtain perfectly mated parts. "Sample 3" is an attempt to correct mating difficulties by optimizing the quality produced by the transfer assembly mold (i.e., by optimizing material flow to uniformly fill cavities by increasing mold flow to speed the filling of cavities, etc.) in the belief that bottle leakage occurred due to an imperfect cylindrical shape in the transfer assembly. Finally, "Sample 4" illustrates an attempt to optimize the uniformity of the cap 18 and particularly the raised elements 22, by improving the cap mold alone.

The test as previously described thus measures the percent leakage visualized past the innermost raised element 22. As detailed in the chart hereinbelow, while the first four "samples" displayed as much as a 44% leakage rate over a period of eight hours, the bottles produced with the seal in accordance with the present invention displayed no leakage:

LEAKS AT THE INNERMOST RAISED ELEMENT (IN %)
TIME OF PRESSURE EXPOSURE

| | 30 MIN | 1 HOUR | 2 HOURS | 4 HOURS | 6 HOURS | 8 HOURS |
|---|---|---|---|---|---|---|
| Sample 1 | 0% | | | 2% | | |
| Sample 2 | 11% | 29% | 33% | 39% | | 44% |
| Sample 3 | 3% | | 16% | | 31% | |

-continued

LEAKS AT THE INNERMOST RAISED ELEMENT (IN %)
TIME OF PRESSURE EXPOSURE

| | 30 MIN | 1 HOUR | 2 HOURS | 4 HOURS | 6 HOURS | 8 HOURS |
|---|---|---|---|---|---|---|
| Sample 4 | 8% | 19% | 27% | 33% | 42% | |
| Sample 5 | 0% | 0% | 0% | 0% | 0% | 0% |
| Sample 6 | 0% | 0% | 0% | 0% | 0% | 0 |

Thus, it will be seen that the apparatus and method in accordance with the present invention results in a bottle suitable for long term transportation and storage of a medicament contained therein, preserving the sterility of same prior to use, while being highly able to withstand handling treatment and environmental variations during transit. The seal created displays good surface tension properties preventing inadvertnet disruption, and is readily resilient so as to adapt to changing pressures, temperatures and forces exerted on the bottle during shipment, while still being easily manipulable by a user to enable easy access to the product when use is desired. The method and apparatus in accordance with the present invention serves to obviate molding, defects inherent in large batch molding runs, while providing an economical and cost efficient alternative to ensuring sterility in bottles of this type in large volume.

The skilled artisan will also appreciate that alternatives to the silicone sealing arrangement are possible. For example, in lieu of forming the raised elements 22 from the same material as forms the cap 18, it may be possible to incorporate the raised elements 22 as rubberized or siliconized components, such as rings which are either co-injected together with the cap 18 or separately formed and thereafter affixed to the interior surface of the cap 18. As with the sealing material 32, the rubberized or siliconized rings would be able to conform to microsurface defects in the components so as to seal the bottle against outside contamination. In this manner, the raised elements 22 themselves would perform a sealing function. However, it will also be apparent that rubberized or siliconized elements 22 may be utilized together with the sealing material 32 to amplify the sealing function provided by the rings 22.

It will be appreciated and understood by those skilled in the art that further and additional forms of the invention may be devised without departing from the spirit and scope of the appended claims, the invention not being limited to the specific embodiments shown.

What is claimed is:

1. A transfer assembly for communicating with a container portion of a bottle, with said container portion for retaining a substance therein, said transfer assembly comprising:

a transfer portion;

a protective cap having a closed end portion and an enclosed interior placeable about the transfer portion for safeguarding the transfer portion against contamination with the environment;

a layer of a fluid sealing silicone material along a sealing area of the transfer portion subject to contact with said protective cap; and one or more ridge elements formed on an area of the protective cap coming into contact with the sealing area of the transfer portion, said one or more ridge elements engaging the layer of fluid sealing silicone material during contact between the protective cap and the sealing area of the transfer portion to form the sealing silicone material into a circumferential protective seal between and adapted to the dimensions of said transfer portion and said protective cap.

2. The transfer assembly of claim 1, wherein the sealing silicone material is applied to the transfer portion.

3. The transfer assembly of claim 2, wherein said sealing silicone material is applied in a band configuration adjacent a base area of the transfer portion.

4. The transfer assembly of claim 3, wherein said band configuration of said sealing silicone material is applied in a width of about 3 millimeters.

5. The transfer assembly of claim 1, wherein said one or more ridge elements are substantially circumferentially formed about the interior of the protective cap.

6. The transfer assembly of claim 1, wherein said one or more ridge elements comprise one or more raised protrusions substantially circumferentially formed on a side wall of said protective cap.

7. The transfer assembly of claim 6, wherein at least one of said one or more raised protrusions comprise a rounded head portion for contact with the transfer portion.

8. The transfer assembly of claim 1, wherein said sealing silicone material comprises silicone having a viscosity of about 12500 ctsk.

9. The transfer assembly of claim 1, wherein said protective seal is formed between the protective cap and the transfer portion adjacent a base area of the transfer portion.

10. The transfer assembly of claim 1, wherein said fluid sealing silicone material has a toroidally-shape and is situated along a circumferential zone of the sealing area of the transfer portion subject to contact with the protective cap and precisely conforming to dimensions of the protective cap and the transfer portion.

11. The transfer assembly of claim 1, wherein said transfer portion includes a fluid communication means for permitting fluid communication with the container portion of said bottle.

12. The transfer assembly of claim 11, wherein said fluid communication means includes a piercing element.

13. The transfer assembly of claim 12, wherein said piercing element is a sharpened needle cannula.

14. The transfer assembly of claim 1, wherein said transfer portion includes a side wall portion and a base portion, with the sidewall portion being adjacent the container portion of the bottle.

15. The transfer assembly of claim 14, wherein said transfer portion further includes a skirt portion extending beyond the base portion, with said skirt portion being engageable with an outside surface of the container portion of the bottle.

* * * * *